(12) United States Patent
Simon

(10) Patent No.: US 11,723,651 B1
(45) Date of Patent: Aug. 15, 2023

(54) SURGICAL DEVICES AND METHODS FOR ACHILLES TENDON REPAIR

(71) Applicant: William H. Simon, Virginia Beach, VA (US)

(72) Inventor: William H. Simon, Virginia Beach, VA (US)

( * ) Notice: Subject to any disclaimer, the term of this patent is extended or adjusted under 35 U.S.C. 154(b) by 0 days.

(21) Appl. No.: 18/162,332

(22) Filed: Jan. 31, 2023

Related U.S. Application Data

(60) Provisional application No. 63/267,364, filed on Jan. 31, 2022.

(51) Int. Cl.
*A61B 17/04* (2006.01)

(52) U.S. Cl.
CPC ...... *A61B 17/0469* (2013.01); *A61B 17/0401* (2013.01); *A61B 2017/0496* (2013.01)

(58) Field of Classification Search
CPC .............. A61B 17/025; A61B 17/0625; A61B 17/0293; A61B 17/0218; A61B 17/0206; A61B 17/02; A61B 17/062; A61B 17/0491; A61B 17/29; A61B 17/0482; A61B 17/0493; A61B 17/0401; A61B 17/0469; A61B 2017/0409; A61B 2017/0496; A61B 2017/0495; A61B 2017/0474; A61B 2017/047
See application file for complete search history.

(56) References Cited

U.S. PATENT DOCUMENTS

| 3,394,700 A | * | 7/1968 | Yamamoto | A61B 17/02 600/233 |
| 3,762,401 A | * | 10/1973 | Tupper | A61G 13/0045 600/227 |
| 3,946,740 A | | 3/1976 | Bassett | |
| 5,209,747 A | * | 5/1993 | Knoepfler | A61B 17/29 606/208 |
| 5,947,982 A | | 9/1999 | Duran | |

(Continued)

FOREIGN PATENT DOCUMENTS

| CA | 2510080 C | 6/2005 |
| WO | 2014092863 A1 | 6/2014 |
| WO | 2018183670 A2 | 10/2018 |

OTHER PUBLICATIONS

Stryker. Cobra Design Features. 2019. 1000902685 Rev B.

(Continued)

*Primary Examiner* — Dianne Dornbusch
(74) *Attorney, Agent, or Firm* — ePatentManager.com; Guerry L. Grune

(57) ABSTRACT

An Achilles tendon repair that provides a minimally invasive surgical procedure that requires at least two medical devices comprising: at least one fascial elevator separator and at least one suture passer elevator separator with a paddle guide that assist with repair of Achilles tendons wherein a fascial elevator separator paddle guide that has a U-shaped portion at a distal end provides separation of a Paratenon from an Achilles tendon and also provides a surgical plane along a designated length of the Achilles tendon that eliminates a possibility of damage to either the Sural Nerve or Saphenous Vein. The suture passer elevator separator also provides for precise placement of multiple locking sutures along the medial and lateral free edge if the Achilles tendon which allows even tensioning of the surgical repair.

22 Claims, 7 Drawing Sheets

(56) References Cited

U.S. PATENT DOCUMENTS

| | | | |
|---|---|---|---|
| 6,051,006 | A | 4/2000 | Shluzas et al. |
| 6,139,563 | A * | 10/2000 | Cosgrove, III .... A61B 17/1285 |
| | | | 606/205 |
| 6,200,327 | B1 | 3/2001 | Assal |
| 8,252,011 | B1 | 8/2012 | Forrester et al. |
| 8,821,518 | B2 | 9/2014 | Saliman et al. |
| 8,936,611 | B2 | 1/2015 | Rush et al. |
| 9,211,118 | B2 | 12/2015 | Gregoire et al. |
| 9,439,647 | B1 | 9/2016 | Bourland, III et al. |
| 9,668,726 | B1 | 6/2017 | Bourland, III et al. |
| 9,700,299 | B2 | 7/2017 | Saliman et al. |
| 9,999,422 | B2 | 6/2018 | Rush et al. |
| 2002/0095178 | A1 * | 7/2002 | Wollmer ................ A61B 17/29 |
| | | | 606/207 |
| 2002/0147456 | A1 | 10/2002 | Diduch |
| 2003/0004513 | A1 * | 1/2003 | Guzman ............ A61B 1/00154 |
| | | | 606/62 |
| 2005/0119531 | A1 * | 6/2005 | Sharratt .................... A61F 2/40 |
| | | | 606/86 R |
| 2009/0012538 | A1 | 1/2009 | Saliman et al. |
| 2009/0131956 | A1 | 5/2009 | Dewey |
| 2010/0179591 | A1 | 6/2010 | Saltzman et al. |
| 2012/0283754 | A1 | 11/2012 | Murillo |
| 2014/0163584 | A1 * | 6/2014 | Rohl .................. A61B 17/0469 |
| | | | 606/144 |
| 2014/0188136 | A1 * | 7/2014 | Cournoyer ......... A61B 17/0401 |
| | | | 606/144 |
| 2014/0222034 | A1 | 8/2014 | Saliman et al. |
| 2014/0276987 | A1 * | 9/2014 | Saliman ............ A61B 17/0401 |
| | | | 606/144 |
| 2015/0313589 | A1 | 11/2015 | Hendericksen |
| 2017/0196552 | A1 * | 7/2017 | Endo ................. A61B 17/0469 |
| 2018/0280018 | A1 | 10/2018 | LaPrade et al. |
| 2019/0159772 | A1 * | 5/2019 | Norton ............... A61B 17/0482 |
| 2020/0187934 | A1 * | 6/2020 | Kelly ................ A61B 17/0469 |

OTHER PUBLICATIONS

Firstpass Mini; Family of Suture Passers. Sellsheet. Smith & Nephew, Inc. Mar. 2019.

Assal, M. Achillon; Minimal invasive Achilles tendon suture system. Reference 119 700. 2006. ND 01521-05-06. Integra Lifesciences Corporation.

Achilles PARS SutureTape With Achilles Midsubstance SpeedBridge Implant System, Surgical Technique. LT1-00100-EN_B. Anthrex, Inc. 2019.

Boin, M., et al. "Suture-Only Repair Versus Suture Anchor—Augmented Repair for Achilles Tendon Ruptures With a Short Distal Stump: A Biomechanical Comparison." Orthopaedic Journal of Sports Medicine, Jan. 2017.

Hofheinz, E. Stryker Launches Cobra Suture Passer for Rotator Cuff Repair. Orthopedics This Week. Mar. 2018. https://ryortho.com/breaking/stryker-launches-cobra-suture-passer-for-rotator-cuff-repair/.

Rotator Cuff Repair. Surgical Procedure. 1000903065 Rev A. Stryker Sports Medicine. 2019. Greenwood City, CO.

FIRSTPASS ST Suture Passer. Sellsheet. Smith & Nephew, Inc. Mar. 2019.

TRUEPASS Suture Passer. Smith & Nephew, Inc. 01077 V1.2013.

Bergig, K., International Search Report. Israel Patent Office. ISA/ILPO. Form PCT/ISA/210. Box A-C. dated May 10, 2023, Jerusalem, Israel.

Bergig, K., Written Opinion of the International Searching Authority. Israel Patent Office.. ISA/KIPO. Form PCT/IS/237, dated May 10, 2023, Jerusalem, Israel.

* cited by examiner

SURGICAL DEVICES AND METHODS FOR ACHILLES TENDON REPAIR

PRIORITY

This application is a nonprovisional filing of and claims priority to U.S. Provisional Application No. 63/267,364 filed Jan. 31, 2022, entitled "Surgical Devices And Methods For Achilles Tendon Repair". The above provided application is hereby incorporated by reference in its entirety.

INTRODUCTION

The present disclosure describes surgical instruments for manipulating sutures and more specifically relates to instruments and associated methods needed for minimally invasive surgical repair of a complete Achille(s) tendon rupture, avoiding passing sutures/needles through the Paratenon and surrounding neuro/vascular structure(s). Most specifically, the present disclosure provides instruments and surgical methods to achieve Achilles tendon repair without the possibility of damage to the paratenon, sural nerve, and/or saphenous vein.

BACKGROUND

In many surgical procedures, such as anterior cruciate ligament (ACL) surgeries of the knee, shoulder instability, and Achilles tendon repairs, sutures are used to close wounds and may be used to repair damaged ligaments and soft tissue. As part of the repair, sutures may be routed through tissues and tendons to stitch and/or hold the tissue together. For the purposes of capturing the tissue and anchoring it to a surgical implant often a suture anchor is utilized.

Known instruments for suture passing typically consist of a piercing portion or needle, which may be curved, and a means for retaining the suture within a portion of the needle to enable the suture to be manipulated and passed through tissue during the repair procedure.

During torn or ruptured Achilles surgeries by more current and relatively new techniques utilize a large Beath Needle to pass suture fiber/tape from outside the body, through the skin and underlying subcutaneous tissues, Paratenon, Achilles tendon and out through the corresponding tissues with a Sural Nerve injury rate of 2-14%, The Sural Nerve that runs along the lateral border of the Achilles tendon is a cutaneous sensory nerve of the posterior lower leg and lateral foot. The Saphenous Vein runs adjacent to the Sural Nerve along its full course and is also subject to injury during the Achilles tendon repair.

As opposed to current minimally invasive approaches to Achilles repair in which a large Beath Needle is placed blindly through the skin, subcutaneous tissues, capture jig, tendon, capture jig and corresponding tissues, this disclosure provides for a direct path through a 3 centimeter incision (skin and Paratenon) with direct repair of the Achilles tendon that completely avoids potential damage to the Paratenon and surrounding neuro/vascular structures. The modified suture passer herein is a suture passer elevator separator that is placed in a newly created surgical plane between the Achilles tendon and surrounding Paratenon to allow for greater ease of access for suture spacing thus minimizing damage to the overlying Paratenon. This approach, however, requires a properly angled specifically designed suture passer which for the purposes of this disclosure is a suture passer elevator separator in order to place the suture(s) in the proper location. Generally, since many portions of the human anatomy include small, curved spaces, it is advantageous to provide the ability to use an indirect path through these spaces to grasp and pass a suture through tissue and/or tendons for a variety of procedures. These procedures include the repair of the capsule and labrum for shoulder instability, procedures in the hip joints, and most importantly for the purposes of this disclosure, the Achilles tendon.

The present disclosure addresses the need for the provision of one or more surgical instruments such that the tool(s) allow precise placement of multiple loop locking sutures of (including fibertape) along the medial and lateral tendon borders. The surgical instruments described are primarily designed for repairing the Achilles tendon, but modifications for other operable repairs are also considered. For current surgical instruments that are used, the suture material is passed from outside the body, through the subcutaneous tissues from one side of the tendon to the other, thereby causing bunching of the tendon as the suture is tied. The level of suture placement with the use of the current surgical instruments is limited to the length of the internal/external jig prongs (3-4 centimeters). (Histological studies have shown the zones of injury to the tendon is up to 4 centimeters on either side of the tendon rupture). The more proximal level of the Achilles tendon is mainly flat, causing bunching of the tendon with tensioning of the suture material using any of the available devices. The present disclosure provides a design that eliminates this bunching effect in that loop locking sutures are placed on each side of the Achilles tendon and more importantly above the zone of injury in healthy tendon, which also ensures providing balanced suture tensioning (meaning the tension on each side of the tendon is the same or very close to an identical tension). These devices and associated surgical technique allow placement of multiple locking sutures in a more proximal site of the Achilles tendon within healthy tendon tissue (compared with current conventional procedures) preventing suture pullout that often occurs due to severely damaged or generally unhealthy tendons in need of repair. Damage to the paratenon/deep fascia, Sural Nerve and/or saphenous vein is essentially eliminated. Previous locking suture tools have been designed to pass suture material via large Beath needles that are passed from outside the body, guided by their jig design through the skin, subcutaneous tissues, paratenon/deep fascia, and finally from one side of the tendon to the other, then back out of the body. This technique places the sural nerve, saphenous nerve, and paratenon at high risk of injury during surgery due to their inherent design. As mentioned above, the use of the loop locking surgical instrument(s) completely avoids and eliminates previous operational difficulties regarding suture pullout from the tendon, surgical damage of the paratenon, Sural Nerve and/or the saphenous vein.)

SUMMARY

The present disclosure provides for the use of two or more newly created surgical tools, where the tool(s) are capable of providing at least three (3) locking sutures (in many cases 5) designed to include locking both the medial and lateral portions on each side of a tendon. As described above, these surgical tool(s) are designed for repairing the Achilles tendon, but other operable procedures may utilize these devices and methodology such as for repair of the quadriceps and patella tendons. The present design provides for reduction and/or elimination of tendon "bunching" and provides for balanced tensioning along each side of the tendon. In addition, the design and associated tools/instruments/devices also reduce and/or eliminate the possibility of tearing or other damage due to (unintentional) improper or uneven tensioning. Damage to the Sural Nerve and/or saphenous vein is essentially eliminated. Previous locking suture tools have been designed to pass the sutures completely from one side of the tendon to the other side causing bunching of the tendon as the suture is tensioned. This tensioning procedure may often cause damage during the operation.

In addition, another component of the present disclosure includes the use of a (Paratenon) fascial separator(s) elevator which when combined with the suture passer elevator separator provides an initial surgical plane that separates the Achilles tendon from the overlying paratenon/deep fascia thus preventing accidental suturing and/or injury to these structures so that blood flow and gliding properties to the underlying Achilles tendon is never disturbed both during and after the surgical repair procedure. This paratenon/fascial elevator tool is designed to help determine the proper location of the surgical repair along the proximal or distal length of the tendon rupture. This tool dictates how high or low along the length of the tendon the actual suture repair (specific location) will take place by utilizing demarcation gradation lines that includes a working shaft of at least 30 cm. Actual suture repair takes place by utilizing additional demarcated gradation lines along the hollow cylindrical shaft of the suture passer elevator separator that is a cylindrical shaft of at least 30-35 centimeters to ensure proper and specific suture placement during the operational procedure. Instead of the current conventional design, this tool provides a curvature at the end of the shaft placed at the furthest distal end portion of the working jaws of the modified suture passer (the suture passer elevator separator) which is shown as a U-shaped paddle portion at this distal end. Prior to use of the suture passer elevator separator device, the surgeon is provided with a (Paratenon) fascial separator(s) elevator that is a paratenon/deep fascial separator with a furthest distal end paddle. The fascial separator elevator and paddle is used prior to the use of the suture passer elevator separator by elevating, providing, and maintaining separation of the paratenon/deep fascia from the underlying Achilles tendon. This initiates the protection of these vital structures from accidental injury during the suture technique. This suture passer elevator separator (Paratenon/fascial separator elevator) has a paddle that also directs and centralizes a freed edge of the Achilles tendon into the open jaws of the suture passer of the present disclosure.

Currently, suture passers allow for passage of the suture from the fixed inferior jaw through the target tissue to the superior working jaw allowing for passage of the suture from a deep portion of the tendon to a superficial portion of the tendon. However, for the present disclosure, the suture passer elevator separator provides a different position of the needle portion of the suture passer elevator separator so that it passes sutures from the fixed top jaw (superficial) through the Achilles tendon (target tissue) to the bottom jaw (deep underside) of the tendon, thereby further protecting all superficial and extremely vital Neuro-Vascular structures. This difference in location and design of the suture passer elevator separator of the present disclosure provides a completely inverted version (180 degrees in opposition) of what is in commercial use today.

Also, the suture passer elevator separator provides at least 3 locking double sutures that allow equal tensioning of the sutures for repair and stabilization of the Achilles tendon in both a medial and lateral direction on each side of the Achilles tendon and also allows for reconnection of torn portions of the Achilles tendon and wherein the locking sutures remain subparatenonous to and away from the Sural Nerve and/or the saphenous vein.

Positioning of the apparatus is in opposition to standard suture passers in that the apparatus with the set of jaws/grasper and the needle passer are positioned 180 degrees in opposition to standard suture passers and allows a thickness equivalent of two sutures/fiber tapes to be passed from a superficial to a deep position of the Achilles tendon (as compared to the) standard suture passers.

More specifically, at least three medical devices for minimally invasive tendon repair are described as follows;
(i) one or more fascial elevator separator(s) comprising a U-shaped paddle guide attached to a distal portion of a cylindrical rod and a proximate handle of the cylindrical rod wherein the fascial elevator separator and U-shaped paddle guide separate a membrane-like areolar structure known as a Paratenon from an Achilles tendon;
(ii) one or more suture passer elevator separators that are tool(s) that maintain separation of the Paratenon from the Achilles tendon and comprises a hollow cylindrical rod with an axial and radial axis to which is attached a distal U-shaped paddle guide with an inverted suture grasping and firing mechanism compared with a conventional suture passer, wherein a set of jaws and a needle is positioned such that the set of jaws and needle enter a prepared surgical plane for one or more sutures provided by the fascial elevator separator and allow the needle to fire and pass through a superficial portion of a tendon to a deep portion of the tendon; and wherein the set of jaws are located along said axial axis of said hollow cylindrical rod in a position between the proximate trigger-handle and directly underneath the distal U-shaped paddle guide to ensure the U-shaped paddle guide maintains separation and guides a free edge of an Achilles tendon into an awaiting set of jaws of the suture passer elevator separator tool(s) to control position and penetration of the sutures utilized for the tendon repair and;
(iii) at least one conventional suture shuttle passer that is utilized to complete the tendon repair.

Here the one or more fascial elevator separator(s) of claim 1, with the U-shaped portion of the facial elevator separator provides separation of a Paratenon from an Achilles tendon and also provides a creates a surgical working plane along a designated length exterior to the Achilles tendon so that one or more modified suture passers allow for passage of the sutures from a ruptured end of the Achilles tendon in a proximal portion of the Achilles tendon (above the zone of injury) toward a knee with passing of the free ends of the proximal locking sutures in a sub-paratenonous manner, through a distal Achilles stump to a calcaneus Suture Bone Anchor so that eventual passage of at least two sutures and/or fiber tapes with the suture passer elevator separator of a locking stitch along a medial and lateral free edge of the tendon preserves blood flow and lubricity to and of the Achilles tendon and eliminates possibility of damage to a Paratenon, Sural Nerve and a Saphenous vein.

In this and additional embodiments, the suture passer elevator separator tool(s) includes an apparatus with both a set of jaws/graspers and a needle passer capable of passing a suture/fiber tape located within and attached to the hollow cylindrical rod shaped shaft so the U-shaped paddle guide portion of the suture passer that is also a facial separator of the Paratenon and said Achilles tendon maintains separation prior to and during passage of the suture/fiber tape along the surgical plane provided by the facial elevator separator and paddle guide and wherein the apparatus with the set of jaws/graspers and the needle passer are positioned such that the suture/fiber tape is passed from a superficial portion to a deep portion of and along the Achilles tendon.

The fascial elevator separator is a paratenon facial elevator that utilizes a U-shaped paddle guide portion with demarcation lines along a shaft of said fascial elevator separator to assist with proper placement of a working surgical plane separating a Paratenon from the Achilles tendon and allows initial placement of the suture/fiber tape along a length of the Achilles tendon as a repair operation proceeds.

The suture elevator separator passer also includes demarcation lines along a length of the solid cylindrical rod shaft that directs a proper position of suture/fiber tape placement during a repair operation.

The suture passer elevator separator and paddle guide has a cylindrical rod shaft with a working shaft that is at least 30 cm in length.

In another embodiment, the suture passer elevator separator provides an ability for the suture/fiber tapes to be placed that can be completely balanced by equal tensioning of the suture/fiber tape on both sides of the Achilles tendon and eliminates bunching and allows for centralization of the tendon inside jaws of the suture passer during an operative process to repair the tendon.

Here the suture passer elevator separator provides at least 3 locking double sutures that allow equal tensioning of the sutures for repair and stabilization of the Achilles tendon in both a medial and lateral direction on each side of the Achilles tendon and also allows for reconnection of torn portions of the Achilles tendon and wherein the locking sutures remain subparatenonous to and away from the Sural Nerve and/or the saphenous vein.

Positioning of the apparatus of the suture passer elevator separator is in opposition to conventional suture passers in that the apparatus with said set of jaws/grasper and the needle of the suture passer elevator separator is positioned 180 degrees in opposition to conventional suture passers and allows a thickness equivalent of two sutures/fiber tapes to be passed from a superficial to a deep position of the Achilles tendon as compared to standard conventional commercially available suture passers.

In a further embodiment, the suture passer elevator separator also comprises a first jaw member and a second jaw member extending from a distal end of the cylindrical hollow shaft, the first jaw member having a suture capturing aperture that is the working movable jaw whereas the channel is for the fixed jaw that allows loading of the suture through the channel and where the first jaw is moveable relative to the second jaw member in a first direction.

The working shaft along a length of the suture passer elevator separator provides a curvature that is inverted by 180 degrees from that of a conventional suture passer that ensures a facial separator paddle is guided along an Achilles tendon and;

wherein the fascial separator elevator paddle separates a Paratenon from the Achilles tendon and centralizes the tendon inside a set of jaws provided by the suture passer elevator separator.

Here the suture passer elevator separator further comprises a handle to manipulate movement of the first jaw member and the second jaw member and a transverse opening of the tissue penetrating member comprises a hook defining a curved surface that faces towards a distal end of the suture passing device.

Here the suture passer elevator separator has a needle that is primarily non-hollow and can also be hollow.

In yet a further embodiment, the second jaw member comprises a transverse surgical plane for pre-loading the device with a length of two sutures and/or fiber tapes and wherein the distal portion of the needle is made of Nitinol.

It is also true that the first jaw member comprises a suture capture member disposed within an opening of the first jaw member for capture of a length of two sutures and/or fiber tapes.

For the suture passer elevator separator of the present disclosure, a distal end of the first jaw member angularly is laterally offset by a first position and wherein a distal end of the second jaw member is angularly laterally offset by a second position, different from the first position.

For this suture passer elevator separator, the angle of the offset of the first jaw member and the second jaw member relative to the longitudinal axis of said shaft is at least 45 degrees and wherein a cross section of the tissue penetrating member is substantially circular.

In another embodiment the present disclosure provides for a medical device kit for Achilles tendon repair comprising:
one or more fascial elevator separator(s) comprising a U-shaped paddle guide attached to a distal portion of a cylindrical rod and a proximate handle of the cylindrical rod wherein the fascial elevator separator and U-shaped paddle guide separate a membrane-like areolar structure known as a Paratenon from an Achilles tendon;

one or more suture passer elevator separators that are tool(s) that maintain separation of the Paratenon from said Achilles tendon and comprises a hollow cylindrical rod with an axial and radial axis to which is attached a distal U-shaped paddle guide with an inverted suture grasping and firing mechanism compared with a conventional suture passer;

one or more large curved suture shuttle passers;
two or more suture bone anchors;
a drill that can accommodate various sizes of suture bone anchors;
a length of sutures and/or fiber tape needed to complete the Achilles tendon repair.

In a further embodiment, the kit and components of the kit are utilized for repair of quadriceps and patella tendons.

In yet another embodiment the suture passer elevator separator includes a camera that is located and mounted on an outer portion of the hollow cylindrical rod in order to provide a more accurate determination of where sutures are to be utilized along either a lateral or medial length portion of the Achilles tendon to ensure direct visualization of suture placement and repair.

In another embodiment a method for repairing Achilles tendons comprises:
preparing a patient for and administering anesthesia and placing the patient in a prone position on an operating room table followed by palpation of the Achilles tendon rupture for locating defects and ends of a tendon tear and/or rupture, wherein a transverse incision is made just proximal to a palpable defect through only a dermis of the patient so that this action is followed by a blunt dissection advanced through subcutaneous tissues while ensuring protection of a Sural Nerve and saphenous vein, wherein the nerve and vein lie just lateral to the Achilles tendon, so that once a paratenon is identified it is sharply incised transversely exposing torn ends of the tendon and surrounding hematoma and wherein the hematoma is evacuated and any frayed torn ends of said tendon are removed without damaging healthy tendon and wherein said proximal end of the tendon is grabbed with at least one Kochers-clamp forceps so that applying tension allows for control of the tendon and so that a paddle guide is passed along both a medial and lateral edge of the Achilles tendon thereby creating a soft tissue surgical plane to stage a suture passer utilizing suture/fiber tape to be passed subparatenonously thereby also preserving vascularity and tendon gliding properties of the Achilles tendon, wherein the suture passer also includes a paddle guide portion that is placed into the surgical plane so that the curved shaped paddle guide portion and an inverted suture grasping and firing mechanism which is a portion of a suture passer elevator separator and guides a side of the ruptured tendon into opened jaws of the suture passer allowing proper placement of at least three locking loop stitches wherein a suture passer needle is loaded with sutures and/or fiber tapes and the paddle guide portion of the suture passer is passed up one side of the tendon to an appropriate depth and wherein the at least three locking loop stitches are then passed equally along each side of the tendon with the fiber tape and/or suture so that when the fiber tape is properly placed, applying tension to a proximal segment of the tendon for at least 5 minutes occurs, bringing the Achilles tendon out to its original length and ensuring equal and balanced tensioning on both sides of the tendon, and;

wherein attention is next directed to both sides of a heel bone just proximal to insertion of said Achilles tendon, wherein two vertical incisions are made on each side of the tendon allowing for dissection to be performed taken down to a bone portion of the heel bone and wherein a calcaneus is then drilled to an appropriate depth depending on size of the suture anchor chosen and a large-curved suture shuttle passer is then placed from a heel incision through a distal tendon stump and into a transverse surgical site so that the curved suture shuttle passer is used to pull one or more proximal suture tapes through a distal Achilles tendon to each of the surgical incision sites on each side of the heel bone wherein an appropriate sized bone suture anchor is loaded with ends of sutures and/or fiber tapes and fixed to the calcaneus so that final surgical repair allows tensioned bringing torn ends of the tendon together wherein the bone suture anchor is locked into place securing sutures and/or fiber tapes into the calcaneus without use of a knot and said paratenon is then sutured back together maintaining its vascularity for tendon healing and proper tendon gliding.

The method for repairing Achilles tendons includes subcutaneous and dermal sutures are placed according to one or more surgeons' preferences.

The method described for repair of the Achilles tendon allows for a patient's wound to be dressed and a posterior splint or cast is applied with an ankle in equines and wherein sutures and/or fiber tapes may be biodegradable so that sutures and/or fiber tapes need not be removed post Achilles repair and wherein bone marrow aspirate and/or use of PRP (platelet rich plasma) that provides progenitor stem cells from a patient undergoing the method wherein the platelets and/or cells are soaked into a patch prior to wrapping the patch around a rupture site of the tendon thereby providing a bioavailable and biocompatible collagen matrix that accelerates full recovery of the Achilles tendon.

The method for repairing Achilles tendons of the present disclosure includes use of an appropriate depth of the suture passer needle loaded with sutures and/or fiber tape is in a range of 70 to 80 centimeters.

Here the method for repairing Achilles tendons includes an appropriate depth of drilling the calcaneus is 15 to 25 millimeters that still depends on the size of the bone suture anchor chosen.

Here passing the suture passer elevator separator with the suture and/or fiber tape through an open incision is accomplished.

In a further embodiment it is possible that preloading the suture passer elevator separator with one or more sutures and/or fiber tapes so that a thickness of the sutures and/or fiber tapes is twice that an original thickness of the sutures and/or fiber tapes.

Methods of Using

In order to employ the use of both a modified loop locking suture passer elevator separator and a fascial elevator with paddle guide, such that these at least two tools are employed to provide a fascial separator to separate the paratenon separator sheath from the Achilles tendon and the modified suture passer tool for providing and locking the sutures/fiber tapes, one such technique is described as follows;

After anesthesia is achieved, the patient is placed in a prone position on the operating room table. The Achilles tendon rupture site is palpated to locate the defect and ends of the tendon tear. A three-centimeter transverse (or longitudinal-Surgeon's preference) incision is made two centimeters proximal (prevents disruption of the Paratenon at the eventual final repair site) to the palpable defect through the dermis only. Blunt dissection is then advanced through the subcutaneous tissues and involves paying particular attention to protect the Sural Nerve and saphenous vein that lie just lateral to the Achilles tendon border. The deep fascia and underlying paratenon is identified and is sharply incised transversely exposing the torn ends of the Achilles tendon and surrounding hematoma. The hematoma is evacuated, and any frayed torn ends are excised to healthy tendon. The proximal end of the tendon is grabbed with one or two Kocher clamp forceps that allows initiation of applying tension and control of the tendon. The present disclosure provides for a specially designed paratenon/fascial separator is then passed along both the medial and lateral edges of the Achilles tendon to elevate and separate the paratenon in a direction away and upward from the Achilles tendon. This creates a surgical working space for the suture shuttle passer device to be passed so that the subparatenon allows for preserving the paratenon's vascularity and for the Achilles tendon to maintain its original gliding properties. These properties are essential to maintain blood supply to the ruptured ends of the tendon and preventing post-surgical adhesions of the tendon. Use of the suture or tape is that of the surgeon's preference. The recommendation is the use of fiber-tape as it has greater resistance that reduces the probability of tendon pullout.

The paddle guide (pre suture passer elevator separator) of the present disclosure is placed into the surgical plane created along the edge of the tendon, so that the lateral edge of the tendon winds up inside the paddle during use. The paratenon suture elevator separator portion on the end of the suture passer then uses the paddle (shuttle) portion to guide the edge of the Achilles tendon into the awaiting open jaws of the suture passer mechanism for guaranteed proper placement of the loop locking sutures or fiber-tapes with each stitch passed. Optimally at least three (3) to five (5) sutures/tapes for making locking loop stitches are provided during the operation. It is important to understand that stiches can be placed along the length of the tendon depending on the tendon quality and/or surgeon's discretion. These sutures/fiber tapes are then passed equally along each side of the tendon with the ability to provide equal tensioning on both sides of the tendon. With the suture/fiber-tape properly placed, a predetermined or determined tensioning tension, is applied to the proximal torn segment for roughly 5 to 10 minutes so that an improved ability to bring the Achilles tendon back to its original resting length can be provided.

At this time during the procedure, if the surgeon prefers a suture/fiber-tape to suture/fiber-tape technique, the same process of elevating the paratenon from the distal stump and placement of loop locked suture on each side of the tendon can be performed with the previously designed suture passer devices. The disadvantage in utilizing these devices and technique is that the tied suture/fiber-tape ends might become located at the incision line which can be palpated during and post-surgery, thereby causing irritation. If delayed healing of the skin or post operative infection occurs, the possibility that the tied and knotted ends of the suture/fiber tape material remain in an undesirable location potentially causing higher risk of exposure and/or infection. This issue then can lead to ultimately requiring a second surgical procedure. This is a very serious post operative complication that can lead to multiple surgeries all avoidable with use of a suture anchor technique for fixing the repair into the heel bone. The use of a bone anchor in the heel allows for the suture to remain mainly intra-tendinous avoiding large palpable knots and decreasing exposure to infections. Biomechanically a proximal suture construct with a distal suture bone anchor to the heel bone has been found to be statistically much stronger than a proximal suture construct to a distal suture construct. Using this technique improves the ability for proper tensioning during the procedure described above.

Attention is now directed to the superior aspect of the posterior aspect of the calcaneus where a 5 to 7 millimeter (depending on the size of suture bone anchor) vertical incision is made along the medial and lateral border of the Achilles tendon. Blunt dissection is then taken down to the bone avoiding any of the vital structures. The calcaneus is then drilled to the proper size and depth depending on the size of the suture anchor chosen. A conventional, curved suture shuttle passer is then placed from the heel incision through the distal tendon stump remaining intra-tendinous to the end of the torn tendon exiting at the transverse incision. The curved suture shuttle passer is then used to pull the two fiber-tape ends on each side the tendon emanating from the end of the proximal tendon rupture, through the distal tendon stump to the small incisions located on each side of the heel bone. By remaining intra-tendinous in the distal stump, injury to the paratenon and the adjacent neuro-vascular vital structures is completely prevented. The properly sized bone suture anchor is loaded with the fiber-tapes and placed into the calcaneus without locking on one side and repeated on the other side in the same surgical manner. With the foot in the maximal plantar flexion position, the fiber-tapes are equally tensioned bringing the torn ends of the Achilles tendon together within the sleeve of the paratenon. The suture bone anchors are then locked into place securing the fiber-tape into the calcaneus in a "knot-less" (free of knots) technique preventing the possibility of large palpable tied knots that could cause irritation or infection. The paratenon, at the transverse surgical incision, is sutured and closed with absorbable suture that will be proximal to the approximated torn tendon ends while maintaining complete pre-op Achilles tendon vascularity for tendon healing and proper tendon gliding. Subcutaneous and dermal sutures are placed according to the surgeon's preference. The patient's wound is dressed in sterile dressings and a posterior splint or cast is applied with the ankle in equinus taking any pressure off the tendon repair. This portion of the present disclosure provides faster healing and rehabilitation with fewer post operable surgical complications due to the biomechanically stronger loop locking stitch in a minimally invasive surgical procedure.

Surgical Technique:

After anesthesia is achieved, the patient is placed in a prone position on the operating room table. The Achilles' tendon rupture is palpated to locate the defect and ends of the tendon tear. A three-centimeter transverse incision is made just proximal to the palpable defect through the dermis only. Blunt dissection is then advanced through the subcutaneous tissues by also paying particular attention to protect the Sural Nerve and Saphenous Vein that lie just lateral to the Achilles' tendon. The Paratenon is identified and is sharply incised transversely exposing the torn ends of the tendon and surrounding hematoma. The hematoma is evacuated, and any frayed torn ends of the tendon are removed from the healthy tendon. The proximal end of the tendon is grabbed with one or two Kochers clamp forceps to apply tension to control the tendon. The special designed paddle guide which is a Paratenon/Fascial separator is then passed along both the medial and lateral edges of the Achilles tendon. This creates a soft tissue plane for the suture passer to be passed subparatenonously preserving its vascularity and tendon gliding properties. The suture passer's which also includes a paddle guide like portion is placed into the created surgical plane and is guided to the side of the ruptured tendon into the open jaws of the suture passer allowing proper placement of the locking loop stitches. With the needle loaded with fiber tape, the device is passed up the side of the tendon to an appropriate depth. Three to five locking loop stitches are then passed equally along each side of the Achilles tendon. With the fiber tape properly placed, tension is applied to the proximal segment for 5 to 10 minutes bringing the Achilles' tendon back to its original length.

Attention is then directed to the sides of the heel bone just proximal to the insertion of the Achilles tendon. Two, 5-millimeter vertical incisions are made on each side of the tendon. Dissection is then taken down to the bone. The Calcaneus is then drilled to the proper depth depending on the size of the suture anchor chosen. A large-curved suture shuttle passer capable of passing the free ends of the looped locking sutures/tapes is then placed from and utilized at the heel incision through the distal tendon stump and into the transverse surgical site.

The suture passer elevator separator includes a paddle so that it functions as a suture passer and elevator separator as one unit and is used to pull the proximal suture tape through the distal Achilles' tendon to each of the surgical incision sites on each side of the heel. The proper sized bone suture anchor is loaded with the ends of the fiber tape and fixed to the calcaneus. The surgical repair is then tensioned bringing the torn ends of the tendon together. The bone suture anchor is locked into place securing the suture fiber tape into the calcaneus in a knot less technique. The Paratenon is then sutured back together maintaining its vascularity for tendon healing and proper tendon gliding. Subcutaneous and dermal sutures are placed according to the surgeon's preference. The patient's wound is dressed, and a posterior splint or cast is applied with the ankle in equinus. This is where it is possible that the use of sutures and/or fiber tapes are biodegradable so that the sutures and/or fiber tapes need not be removed post Achilles repair and where a bone marrow aspirate and/or use of PRP (platelet rich plasma) that provides progenitor stem cells from a patient undergoing this method is provided with platelets and/or cells soaked into a collagen patch prior to wrapping the collagen patch around a rupture site of the tendon thereby providing a bioavailable and biocompatible collagen matrix that accelerates full recovery of the Achilles tendon.

These and other features and advantages will be apparent from a reading of the following detailed description and a review of the associated drawings. It is to be understood that both the foregoing general description and the following detailed description are explanatory only and are not restrictive of any aspects of the disclosure and related invention, as claimed.

BRIEF DESCRIPTION OF THE DRAWINGS

The disclosure will be more fully understood by reference to the detailed description, in conjunction with the following figures, wherein.

DETAILED DESCRIPTION

Figure 1A:
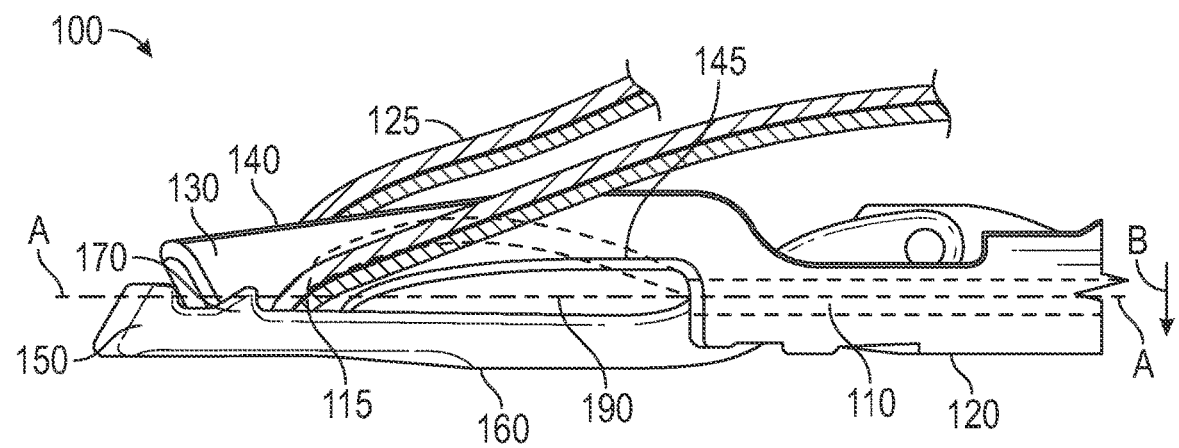
FIG. 1A illustrates a side view of an exemplary angled suture passer of this disclosure with the jaws in a closed position.

In the description that follows, common components have been given the same reference numerals, regardless of whether they are shown in different examples. To illustrate example(s) in a clear and concise manner, the drawings may not necessarily be to scale, and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Referring now to FIG. 1A, there is shown a side view of a suture passer elevator separator [100], wherein a first plane is defined as parallel to the longitudinal axis A and parallel to the view shown such that the direction B is perpendicular to the first plane. A second plane is also defined and relied upon (later in this discussion) that is also parallel to the longitudinal axis, and perpendicular to the first plane, and best shown in FIG. 2A. The suture passer elevator separator [100] has an elongate shaft [120] extending from a handle (not shown). The working shaft has a length of 30 to 35 cm with depth markings along the shaft for precise suture [125] placement along edges of the tendon. The increased length allows the hand mechanism to be extended beyond the heel portion during the procedure. A lumen [110] extends through the shaft [120]. A distal end of the shaft [120] may curve downward to terminate in a distally-extending upper jaw [140]. Alternatively, upper jaw [140] may be a separate element (not shown), coupled to and extending distally from a distal end of the shaft [120], and may be coupled so as to be fixedly attached to the stationary jaws. Upper fixed jaw [140] may define an upward curve at the proximal end so as to define an opening or gap [190] at the proximal end of the jaw between the two facing surfaces of the upper fixed and lower working jaw ([140] and [160] respectively). This provides clearance for tissue disposed therein to be grasped. Upper fixed jaw [140] may comprise an elongate body with an elongate channel [145] disposed therein, and as shown in FIG. 1A, the jaw defines a first curve along the first plane, curving initially away from longitudinal axis at the proximal end, curving back towards and across the longitudinal axis at the tip or distal end [130]. This first curve along the first plane aids to keep the distal tips of the two jaws [140, 160] closer together and also aids in reducing stresses by allowing some curvature on a needle retained within the elongate channel (shown in dotted lines on FIG. 1A) and described in more detail below. This first curve also aids in directing the needle [180] as it extends towards the lower working jaw [160]. A substantially linear lower working jaw [160] is attached to the shaft [120] such that the lower working jaw [160] and the upper fixed jaw [140] may be biased in the closed position, as shown. In working examples, the lower working jaw [160] may pivot about a longitudinal axis (A) relative to the shaft [120] (as shown) or, alternatively, the connection between the upper fixed jaw [140] and the lower working jaw [160] may be a reciprocating or cam system wherein the lower working jaw [160] is movable relative to the upper fixed jaw [140]. A length of the lower jaw [160] is selected such that it extends distally beyond the upper jaw [140]. In examples, the diameter of the suture passer [100] is at least 4-8 mm in diameter or is otherwise selected to allow for the internal working mechanism to operate. The upper fixed jaw [140] also includes a transverse channel [115] (best seen in FIGS. 1B and 2B) for initial retention of at least two lengths of two sutures [125] therethrough in preparation for stitching the sutures/fiber tapes [125] simultaneously through soft tissue and subsequently capturing the sutures [125].

A tissue receiving area [190] is defined between the upper fixed jaw [140], the lower working jaw [160], and the distal end of the shaft [120]. Jaws are shaped such that the tissue receiving area [190] is larger towards the proximal end of the jaws as a relief for tissue disposed therein, while still maintaining a smaller distance between the two jaws towards the distal ends of jaws, adjacent the channel [115]

to aid in a reliable suture capture during operation. Here, a width of the distal end [150] of the lower working jaw [160] is selected to be larger than a width of the distal end [130] of the upper fixed jaw [140], such that the upper fixed jaw [140] is housed within opposing upwardly extending protrusions or teeth [170] of the lower working jaw [160] when the suture passer [100] is in the closed position. The location of the teeth helps to enclose and control the tissue within the jaws, while not overly compressing the tissue that the needle [180] has to penetrate through, making the action of the needle [180] more reliable for guiding and stabilizing. Notably, in the closed position, the teeth [170] do not block the channel [115] in the upper fixed jaw [140] so that the suture passer [100] can be passed effectively through a surgical incision when in the closed position. Teeth [170] are distally spaced from the channel [115].

Figure 4A:
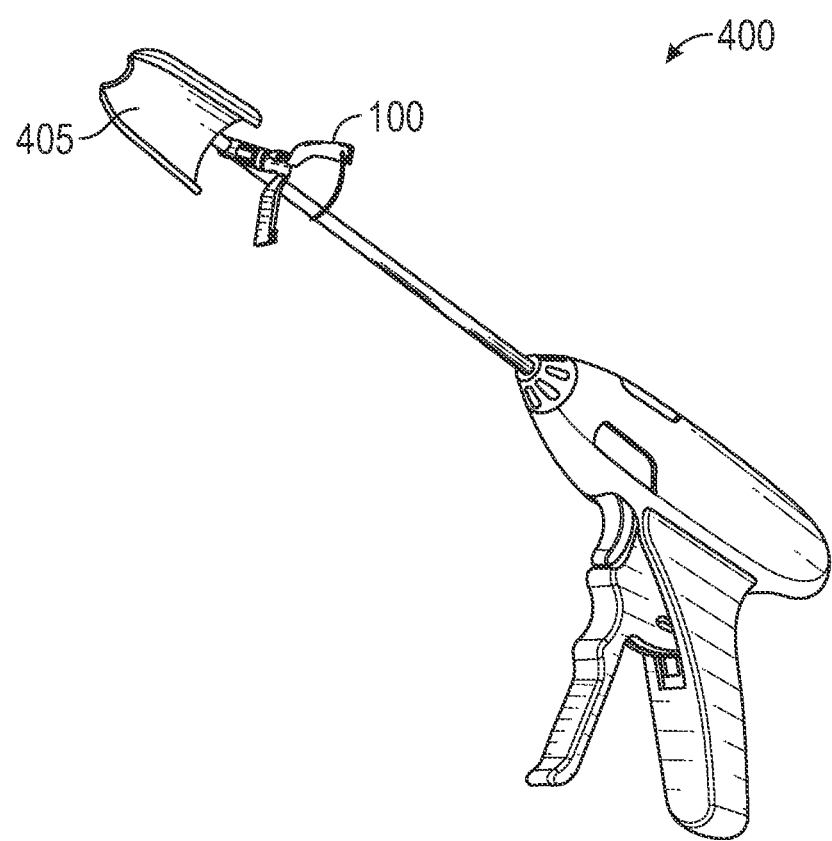
FIG. 4A illustrates a suture passer elevator separator equipped with a paddle guide that provides a paratenon/deep fascia elevator.
Figure 4B:
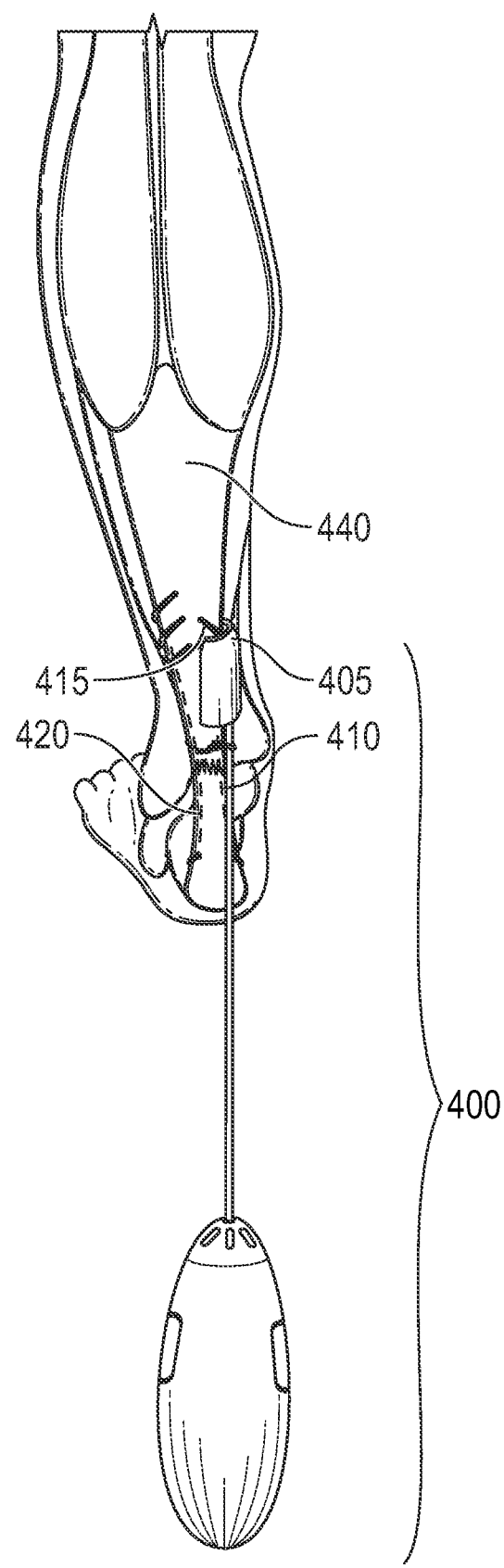
FIG. 4B illustrates the suture passer elevator separator with paddle guide positioned on a lateral border along the Achilles tendon.

In various examples, not shown, the handle is an in-line type handle. The handle may include an opening for accommodating a user's fingers and is shown in FIGS. 4A and 4B. In alternative examples, the handle does not include such an opening, and the user's fingers simply fit around the handle. The handle may also include one or more actuators to open/close the lower working jaw [160] relative to the upper fixed jaw [140] and/or to extend/retract the needle [180]. For example, the actuator(s) may be in the form of a thumb activated slider which may be moved distally toward from the handle to activate the suture passer [100]. The needle passes from the fixed upper jaw (140) to the lower working jaw (160). The actuator may be biased by suitable means, such as a spring, to default to a closed/retracted position when an application force is removed, for example, when a user removes pressure from a finger or thumb. Here the needle [180] could be shifted between positions to grab two sutures to be passed simultaneously through the Achilles tendon. The preference is to use two portions of a single 2 mm fibertape suture [125] simultaneously, allowing for the sutures [125] to be applied in a loop locking stitch to the border of the tendon through a single entrance into the surgical incision site. Fibertape sutures are a wider suture construct than the #2 standard round suture and reduce tissue cut-through when surgically repairing poor quality torn Achilles tendon tissues.

Figure 1B:
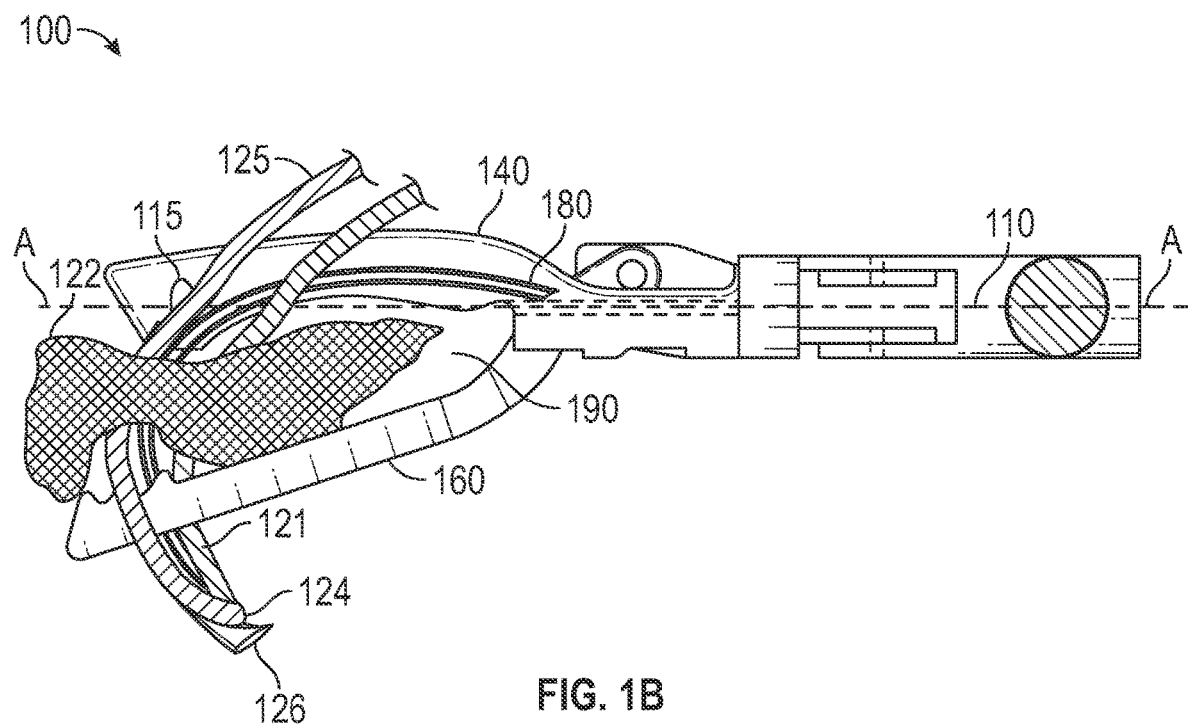
FIG. 1B illustrates the suture passer of FIG. 1A with the jaws grasping tissue and the needle extending through the tissue.

Turning now to FIG. 1B, it can be seen that a curved needle [180] for passing the sutures [125] through soft tissue [122], such as Achilles tendon tissue, is configured to be axially movable within and extendable from the lumen [110] of the shaft [120] and a needle [180] in the upper fixed jaw [140], such that the needle tip [126] may be moved from a retracted position, wherein the needle [180] is withdrawn or shielded from the tissue receiving area [190], to an extended position, wherein the needle [180] is displaced through an opening in the lower working jaw [160] and through the soft tissue [122]. The needle [180] may be housed along a portion of the upper jaw [140] in the first position with the needle tip adjacent to and slightly retracted from the transverse channel [115]. The upper fixed jaw [140] may comprise a channel [145] shown in FIG. 1A—along its length for housing and sheltering the needle [180] in the first position, the channel having a distal ramp [141] (FIG. 2B) adjacent the transverse channel [115] of the upper fixed jaw [140] so as to direct the needle [180] towards the transverse channel [115] to reliably pick up the lengths of sutures [125] disposed within the transverse channel [115]. Since the needle [180] is curved in its unstressed configuration (described later), which defines the needle trajectory as it extends out of the channel [145], the ramp [141] is not considered a means for significantly altering the extended trajectory of the needle, merely a local control surface to aid in reliable suture capture near channel [115]. As the needle extends and is released to its resting state, the needle is shown in FIG. 1B to curve approximately perpendicular to the longitudinal axis A and potentially even in a proximal direction. It follows therefore that a ramp [141] may not be necessary and no ramp or an open distal end [130] of the upper jaw [140] may suffice. Counter to this, should the needle [180] be produced without a preformed curve as disclosed, a ramp [141] or bumper may be required to induce a needle trajectory, which would predominantly extend linearly from the ramp [141] and not continue to curve approximately perpendicular to the longitudinal axis A and potentially in a slight proximal direction as shown in FIG. IB. As shown in FIG. 1B, the needle tip [126] is more proximally disposed relative to the suture channel [115]. This curved trajectory keeps the needle tip [126] close to the lower working jaw [160] rather than extending away from it, which helps to reduce injury that the needle tip [126] may cause to the tissue as it moves through and away from the lower working jaw [160]. A housing may be used which has a covered portion [142] to better grasp tissue and protect the needle [180]. Housing [140] may be curved, along the first plane discussed earlier relative to FIG. 1A to better guide the needle [180] and improve engagement reliability with a suture capture aperture of lower working jaw [160]. A covered portion [142] may help retain the preformed needle [180] within the housing.

Further at least a distal portion of the needle [180] is comprised of a super-elastic material, such as nitinol, and has a generally circular cross-section. A circular cross section provides some added lateral stiffness and helps the needle [180] retain its path as it extends through the tissue and lower working jaw [160]. The needle itself [180] may be substantially hollow or substantially non-hollow. The needle [180] may be tapered and may have a length of smaller diameter or non-circular cross section adjacent the distal tip of the needle and a length of larger diameter proximally extending therefrom. This may allow for easier insertion though the suture capture aperture [134], described below. The super-elastic nature of the material allows the needle [180] to be disposed in a generally linear configuration relative to its preformed shape while placed in the retracted position so as to be readily conformed to the housing within the upper fixed jaw [140], and then returns to a form closer to the preformed, curved configuration during the displacement of the needle [180] from the retracted to the extended position.

In the fully extended position of the needle [180], the sutures or fiber tapes [120] that have been drawn through the tissue [122] forms a suture/tape portion [121] which protrudes from and is disposed above the lower working jaw [160]. In our example, the suture/tape portion [121] may form a looped configuration.

Still referring to FIG. 1B, the lower working jaw [160] may be actuated by the handle to move to a closed position to enable the suture passer [100] to immobilize and stabilize the tissue [122] between the lower working jaw [160] and the upper fixed jaw [140]. With the tissue [122] grasped between the lower working jaw [160] and the upper fixed jaw [140], the needle [180] may be deployed by actuation of the needle deployment member or trigger in the handle to the extended position. The needle [180] is advanced axially toward the distal end of the suture passer [100] such that a transverse opening [124] of the needle [180], which may be in the form of a distally facing hook. As the needle [180] is advanced in a generally distal direction through the Achilles tendon passing the suture back toward its resting state followed by retraction. The protrusions or teeth [170] assist in retaining the tissue [122] within the tissue receiving area [190] as the needle [180] advances through the soft tissue [122]. In order to aid in maintaining a reliable needle [180] and thereby suture trajectory though the tissue, the needle cross section is preferably a circular cross section, and the target tissue is kept stabilized within the grasping mechanism so that the needle is easily passed through the tissue.

Figure 2A:
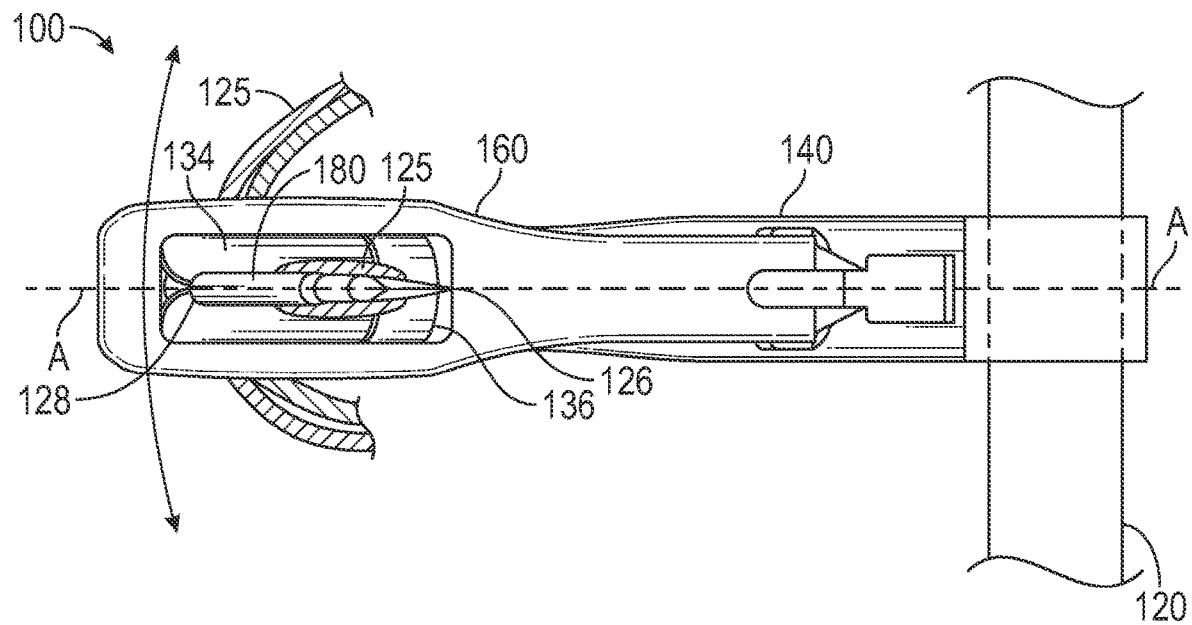
FIG. 2A illustrates a top view of the suture passer of FIG. 1B with the tissue removed.
Figure 2B:
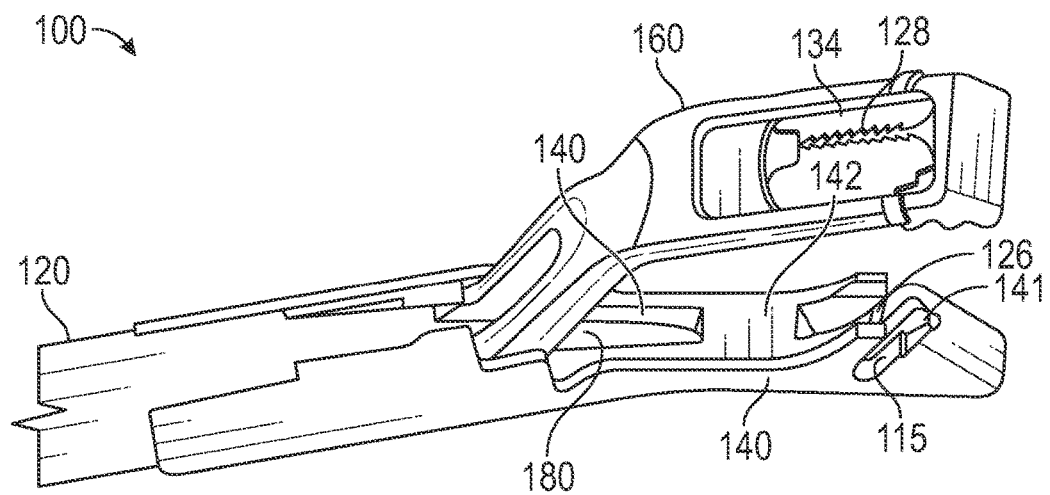
FIG. 2B illustrates the underside of a suture passer with the jaws in an open position and the needle in a retracted configuration.

FIG. 2A illustrates the suture passer elevator separator [100] of FIG. 1B in a bottom surface view. The suture capture member [134] may be in the form of a removable cartridge or may be an integrated structural component of the lower working jaw [160]. A further detailed description and examples of suture capture members can be found in U.S. Pat. No. 9,211,118, the complete disclosure of which is incorporated herein by reference. In examples, the suture capture aperture [134] is comprised of high-temper, spring steel material and capable of capturing 2 sutures/tapes through the opening.

In one embodiment, the angulated grasping jaws, lower working jaw [160] and upper fixed jaw [140], are laterally angled or curve away from the longitudinal axis (A) of the shaft [120] along the second plane. As viewed from above, the lower working jaw [160] and the upper fixed jaw [«] may be angled either to the left (as shown) or to the right, from 45 up to 90 degrees from the longitudinal axis (A) of the shaft [120]. For other devices that target alternative areas of the patient, larger or smaller angles and offsets are envisioned, and generally speaking, this angle and lateral offset may be any non-zero value that improves target tissue access through a curved space, given the procedure and patient anatomy. In alternative embodiments (not shown) each jaw may have a slightly different angled offset from each other, so as to be staggered and potentially adjust for an altered path of the needle [180] as it extends through the tissue [122]. Needle [180] may continue along a reliable trajectory along the longitudinal axis; however, it may be laterally offset relative to a suture capture aperture [128].

Returning now to FIGS. 1A-2A, in operation, the user (e.g., surgeon) may insert the suture passer elevator separator [100] mechanism through a minimally invasive incision. Generally, the suture passer elevator separator [100] mechanism is preloaded with sutures [125] (FIG. 1A). The suture [125] may be a grabbed by a suture passer elevator separator mechanism (as shown in more detail in FIGS. 2A and 2B) with a suture [125] attached, or it may be a suture [125] or a fiber tape that has already been positioned within the upper fixed jaw [140]. Once the suture passer elevator separator [100] is near the tissue [122] to be sutured/taped, the suture passer elevator separator [100] is actuated so that the tissue [122] may be positioned between the upper fixed jaw [140] and the lower working jaw [160]. This target tissue [122] is grasped at a location offset from the working axis of the suture passer elevator separator [100], the distal end of the suture passer, having a curved or angled portion so as to better access this target tissue [122]. Once the target tissue [122] is stabilized the needle [180] should then be actuated to pass the suture through the stabilized tendon. With the needle tip [126] and the sutures [125] drawn through soft tissue [122], the actuation of the needle [180] continues until the needle [180] advances into and through the opening [136] in the lower working jaw [160] (FIG. 2A). Concurrently, the needle [180] and the sutures [125] are also directed through the aperture [128] of the suture capture member [134].

In summary a major difference between a current conventional suture passer and that designed and created by necessity to perform the minimally invasive Achilles repair operation herein described is that the present disclosure describes a suture passer that provides an inverted position of the mechanism used to allow for the necessary operation of the entire instrument. In accomplishing this task, the suture passer mechanism of the suture passer elevator separator has an angular capacity to pass sutures at an angle of from 45 up to 90 degrees from the longitudinal axis (A). Using this unconventional modified suture passer elevator separator together with the described and shown in FIGS. 3, 4A and 4B below, it is possible to provide an operation that avoids essentially all the pitfalls of any previously known methods to repair the Achilles and other ruptured/torn tendons.

Figure 3:
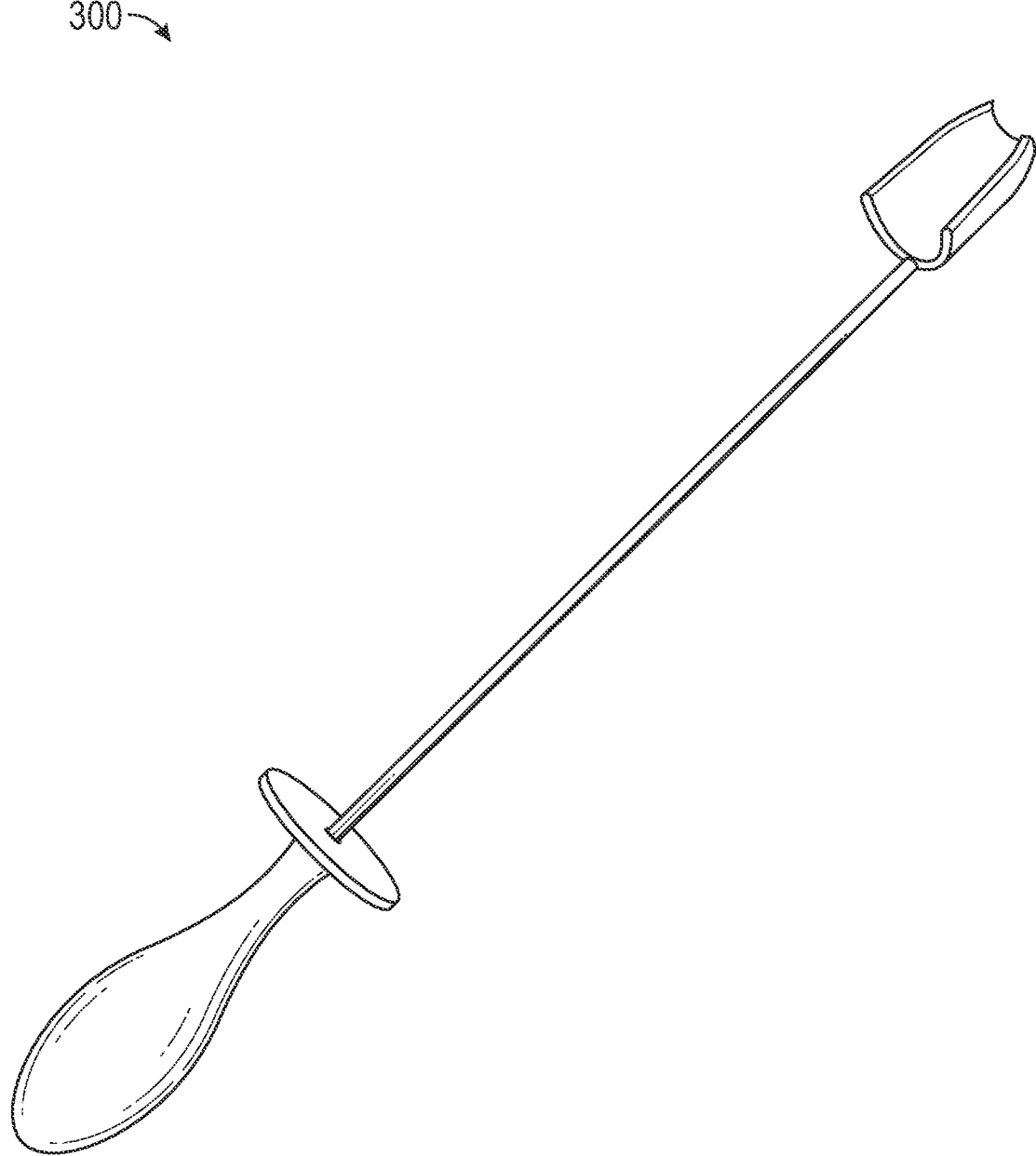
FIG. 3 illustrates a elevator fascial separator with paddle guide for Paratenon sheath separation and elevation.

FIG. 3 is a schematic representation of a fascial elevator separator and paddle guide [300] for a paratenon separation from the Achilles tendon thereby preserving vascularity and mobility of the tendon to minimize potential damage during operative repair for minimally invasive Achilles tendon repair. The fascial elevator separator and paddle guide [300] is a specially designed Paratenon fascial elevator to separate and isolate the Achilles tendon in order to create a surgical plane/pathway/channel for the suture passer elevator separator [100], thereby protecting the Paratenon and surrounding tissue from injury. The Paratenon is a highly vascularized tissue, having visceral and parietal layers but no true tendon sheath. The paratenon produces a lubricating fluid which allows for the tendon to glide, thus preventing friction. The paddle guide [200] allows the paratenon to maintain vascularity to the tendon for healing and maintenance of motion during and post operation. Although the Achilles tendon does not have a true tendon sheath, the paddle guide [200] can be also used on tendons having a sheath, such as the quadriceps tendon and patella tendon.

FIG. 4A provides a suture passer elevator tool [400] equipped with both the ability to provide for maintaining separation of the paratenon from the Achilles tendon via an elevator equipped with a paddle guide [405] and passing sutures during the repair operation. This suture passer elevator tool [400] includes a paddle like portion that includes a fascial separator (paddle) guide along the length of the shaft placed appropriately [405] as shown. The fascial separator guide portion [405] guides the free edge of the Achilles tendon into the awaiting open jaws of the suture passer portion for proper suture [125] placement along the border of the tendon both medially and laterally. For all of the description above and within this disclosure, the suture passer elevator tool [400] must be placed directly behind the paratenon fascial separator to ensure that the surrounding paratenon tissue is either minimally damaged or left completely undamaged. The position of the suture passer elevator tool [400] on the medial [410] and lateral [420] borders of the Achilles tendon [440] is best shown as provided in FIG. 4B. Here the placement of the fascial separator (paddle) guide [405] portion together with the suture passer portion [415] on the tendon is more clearly shown. The suture passer with elevator tool [400] is shown used along the medial border [410] of the Achilles tendon [440}. Either the same tool which can be rotated to the lateral border [420] or a separate tool can be used to accomplish the same function along the lateral border [420] as is shown along the medial border [410].

Figure 5:
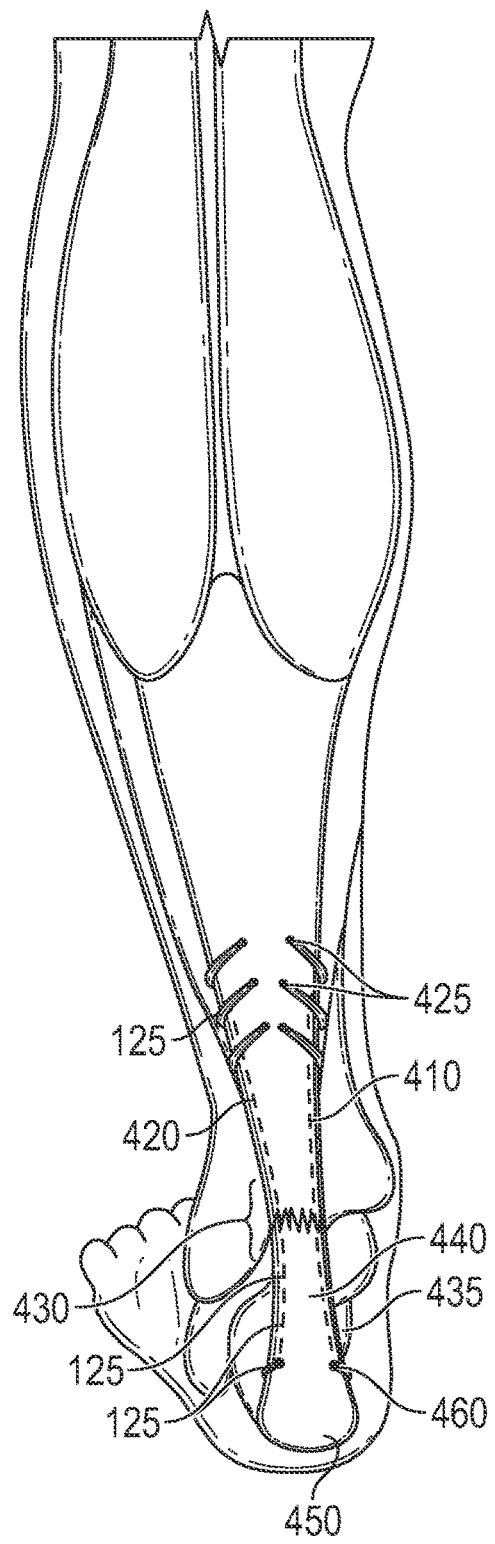
FIG. 5 illustrates a completed Achilles tendon repair, in accordance with the present disclosure.

FIG. 5 illustrates a completed channel-assisted minimally invasive Achilles tendon repair [400] having loop locking stitches [425] provided by fibertape(s) as a construct along the medial border [410] and lateral border [420] of the Achilles tendon [440]. The repair is completed using a pair of three (3) to five (5) Loop Locking Stitches per Girth Hitch above the zone of injury [430] for even and balanced tensioning of the tendon during the tendon repair. A larger, curved modified suture passer (shown as 100) design is necessary to allow for the sutures/fiber tapes to be passed through the distal stump of the Achilles tendon to be eventually secured to the calcaneus [450] (heel bone). In this manner, which has also never before been accomplished for an Achilles tendon repair operation, it is possible to provide intra-tendinous sutures [435] through the end of the tendon tear thereby securing the sutures using a knotless suture-anchor technique [460]. This keeps the fibertape(s) mainly within the Achilles tendon [440] avoiding any adhesions and any possible risk of infection. The use of the Suture-Anchor technique has shown a 116% lower displacement and a 45% greater load to failure versus Suture-Only repair, while leaving no palpable tied knots at the incision site. Suture-Anchor augmented repairs performed on Achilles tendon ruptures with a short distal stump are bio-mechanically stronger than Suture-Only repairs as earlier published (Boin, M., et al., The Orthopedic Journal of Sports Medicine, January 2017).

As the needle [180] is passed during repair from the superficial fixed upper jaw [140] to the deeper working lower jaw [160] as a result of using the three tools developed for this operation and another critical feature of this disclosure, it has become possible to completely avoid medial injury to the Sural Nerve, Saphenous Vein, and Posterior Tibial Nerve. The completed procedure is achieved through a 3 cm transverse incision and results in no proximal bunching of the tendon, and greater suture fixation and tensioning of repair.

Figure 6:
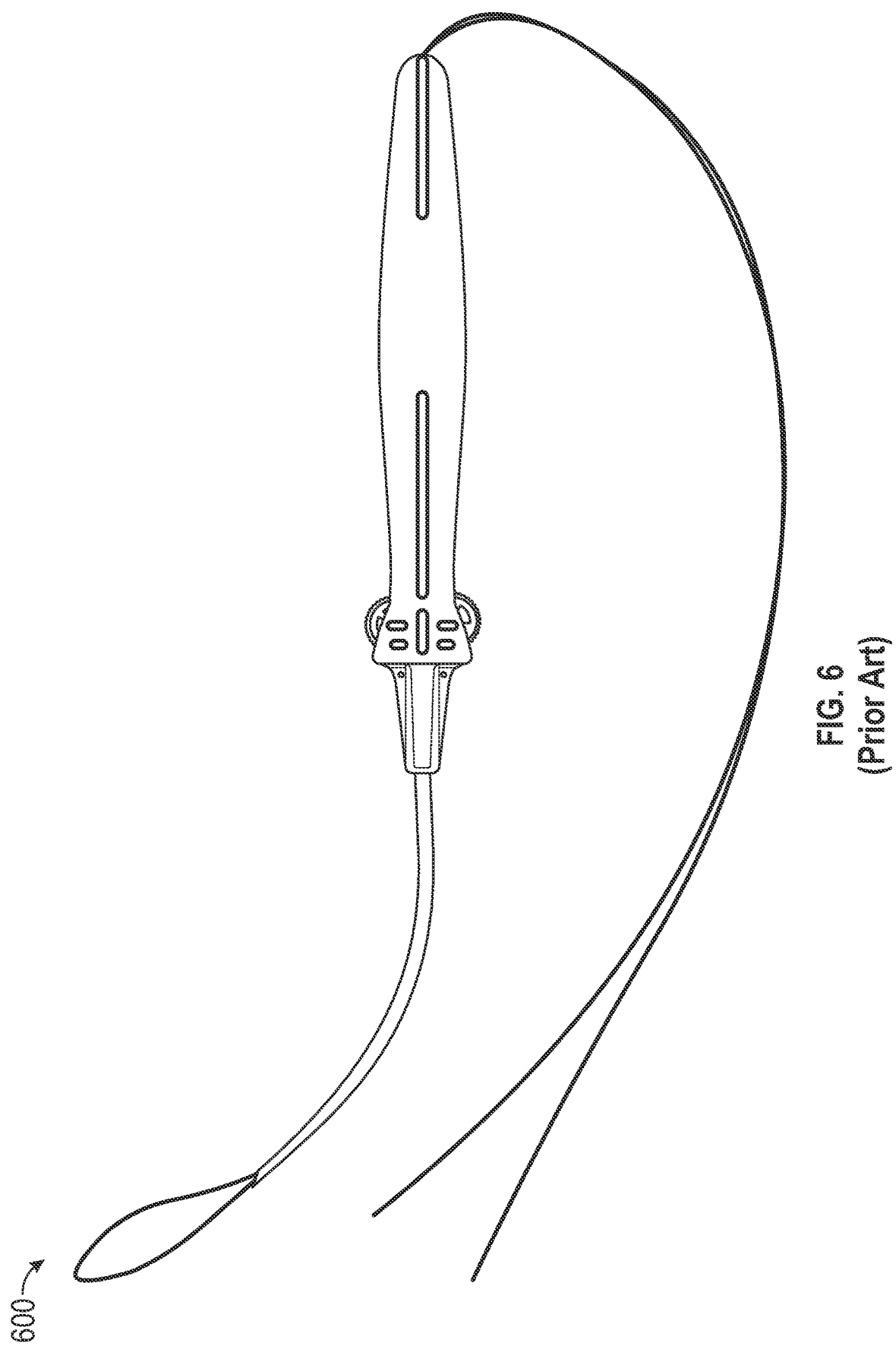
FIG. 6 is illustrative of an example of a suture shuttle passer as described herein and known in the art.

FIG. 6 illustrates an example of a conventional and commercially available suture shuttle passer (600) that is utilized to complete the non-invasive tendon surgical repair as described above. This conventional suture shuttle passer (600) can be supplied in a kit with the other two (2) tools;
  (i) the fascial elevator separator and
  (ii) the suture passer elevator separator or separately; depending on the needs of the surgeon or an offering by those manufacturing the devices.
  The suture shuttle passer (600) as shown and deviations thereof is available and known to those of skill in the art.

While this disclosure has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

What is claimed is:
1. At least three medical devices for minimally invasive tendon repair comprising;
  (i) one or more fascial elevator separator(s) comprising a U-shaped paddle guide portion attached to a distal portion of a cylindrical rod and a proximate handle attached to said cylindrical rod wherein said one or more fascial elevator separator(s) and U-shaped paddle guide portion separate a membrane-like areolar structure known as a Paratenon from a n Achilles tendon;
  (ii) one or more suture passer elevator separator(s) that maintains separation of said Paratenon from said Achilles tendon and comprises a hollow cylindrical rod with an axial and radial axis with an attached distal U-shaped paddle guide and with an inverted structure with respect to a longitudinal axis of said hollow cylindrical rod that includes a grasping and firing mechanism and a set of jaws and a needle so that said grasping and firing mechanism is controlled with a proximate located trigger-handle so that the needle and one or more sutures and/or fiber tapes can follow along a surgical plane between said Achilles tendon and said Paratenon, wherein said needle and said sutures fire and pass through a superficial portion of said Achilles tendon to a deep portion of said Achilles tendon; and wherein said set of jaws are located along said axial axis of said hollow cylindrical rod in a position between said proximate located trigger-handle and directly underneath said distal U-shaped paddle guide wherein said U-shaped paddle guide maintains separation and guides a free edge of said Achilles tendon into said set of jaws of said one or more suture passer elevator separator(s) that controls position and penetration of said one or more sutures and/or fiber tapes deployed for said Achilles tendon repair and;
  (iii) at least one suture shuttle passer that is deployed to complete said tendon repair.

2. The one or more fascial elevator separator(s) of claim 1, wherein said U-shaped paddle guide portion of said one or more fascial elevator separator(s) provides separation of said Paratenon from said Achilles tendon and also provides said surgical plane along a designated length exterior to said Achilles tendon so that one or more suture passer elevator separator(s) allow for passage of said one or more sutures and/or fiber tapes from a ruptured end of said Achilles tendon in a proximal portion of said Achilles tendon above a zone of injury toward a knee wherein a suture loop is passed through said Achilles tendon and free ends of said one or more sutures and/or fiber tapes are passed through said suture loop to form one or more proximal looped locking stiches per girth hitch in a sub-paratenonous manner, through a distal stump to a calcaneus suture bone anchor, so that eventual passage of at least one or more sutures and/or fiber tapes with said one or more suture passer elevator separator(s) provide for implementation of one or more proximal looped locking stitches per girth hitch along a medial and lateral free edge of said Achilles tendon to preserve blood flow and lubricity to and of said Achilles tendon and eliminates possibility of damage to a Sural Nerve and a saphenous vein.

3. The one or more suture passer elevator separators of claim 1, wherein said set of jaws are graspers and include a needle passer capable of passing said one or more sutures and/or fiber tapes, along and through a free edge of said Achilles tendon wherein free ends of two strands of said sutures and/or fiber tapes are passed through a formed suture/fiber tape loop that allows for creation of said one or more looped locking stiches per girth hitch and wherein said one or more suture passer elevator separators acts as a fascial separator of said Paratenon and said Achilles tendon and maintains said separation prior to and during passage of said one or more sutures and/or fiber tapes along a channel provided by said one or more fascial elevator separator(s) and U-shaped paddle guide and wherein said one or more suture passer elevator separator(s) with said graspers and said needle passer provides equal tensioning along both a medial and lateral side of said Achilles tendon when said sutures and/or fiber tapes are passed from said superficial portion to said deep portion of said Achilles tendon.

4. The one or more fascial elevator separator(s) of claim 1, wherein said one or more fascial elevator separator(s) is a paratenon fascial elevator separator and wherein said U-shaped paddle guide portion includes a one or more demarcation lines along said cylindrical rod of said one or more fascial elevator separator(s) to assist with proper placement of said surgical plane that separates said Paratenon from said Achilles tendon and directs initial placement of said one or more sutures and/or fiber tapes along said designated length of said Achilles tendon.

5. The one or more suture passer elevator separator(s) of claim 1, wherein said one or more suture passer elevator separator(s) includes one or more demarcation lines along a length of said hollow cylindrical rod that directs a proper position of said one or more sutures and/or fiber tapes for said one or more suture passer elevator separator(s) placement during said Achilles tendon repair.

6. The one or more suture passer elevator separator(s) of claim 1, wherein said hollow cylindrical rod is a working shaft that is at least 30 cm in length.

7. The one or more suture passer elevator separator(s) of claim 1, wherein said one or more suture passer elevator separator(s) provides an ability for said one or more sutures and/or fiber tapes to be accepted on each side of a proximal portion of said Achilles tendon in a manner by which balance is achieved by equal tensioning of said one or more sutures and/or fiber tapes and eliminates bunching.

8. The one or more suture passer elevator separator(s) of claim 3, wherein said one or more suture passer elevator separator(s) provides at least three locking girth hitch stiches that allow equal tensioning of said Achilles tendon with sutures to repair and stabilize said Achilles tendon along both a medial and lateral direction of said Achilles tendon and wherein said locking girth hitch stiches of said sutures and/or fiber tapes remain subparatenonous to and away from a Sural Nerve and/or a saphenous vein.

9. The one or more suture passer elevator separator(s) of claim 3, wherein wherein said graspers and said needle passer of one of said one or more suture passer elevator separator(s) is positioned 180 degrees in opposition to another suture passer of said one or more suture passer elevator separator(s) and allows a thickness equivalent of two sutures and/or fiber tapes to be passed from the superficial to the deep position of said Achilles tendon.

10. The one or more suture passer elevator separator(s) of claim 1, wherein said set of jaws have a first jaw member and a second jaw member extending from a distal end of said hollow cylindrical rod, said first jaw member being a working movable jaw, having a suture capturing aperture and a second jaw member that is a fixed jaw that allows for loading of one or more sutures/fiber tapes through a channel, wherein said first jaw member is moveable relative to said second jaw member, wherein both first and second jaw members are part of a working shaft provided by said hollow cylindrical rod so that a complete suture passer elevator separator has an inverted grasping and firing mechanism along with said set of jaws and needle with respect to a longitudinal axis of said hollow cylindrical rod and provides a fascial separator U-shaped paddle guide that is guided along an Achilles tendon; and wherein said fascial separator U-shaped paddle guide elevates and separates the Paratenon from said Achilles tendon and centralizes said Achilles tendon inside said set of jaws.

11. The one or more suture passer elevator separators of claim 10, further comprising the proximate located trigger handle to manipulate movement of said first jaw member and said second jaw member.

12. The one or more suture passer elevator separators of claim 10, wherein a transverse opening of a tissue penetrating member comprises a hook defining a curved surface that faces towards a distal end of said suture passer elevator separator that also functions as a suture passing device.

13. The one or more suture passer elevator separators of claim 10, wherein said needle that is utilized by said one or more suture passer elevator separators is primarily non-hollow and wherein said needle can also be hollow.

14. The one or more suture passer elevator separators of claim 10, wherein said second jaw member comprises a transverse channel for pre-loading the device with a length of two sutures and/or fiber tapes for said one or more suture passer elevator separators and wherein said distal portion of said needle comprises Nitinol.

15. The one or more suture passer elevator separators of claim 10, wherein said first jaw member comprises said suture capturing aperture disposed within an opening of said first jaw member to capture a length of two sutures and/or fiber tapes for said one or more suture passer elevator separators.

16. The one or more suture passer elevator of claim 10, wherein a distal end of said first jaw member is angularly laterally offset by a first position and wherein a distal end of said second jaw member is angularly laterally offset by a second position, different from said first position.

17. The one or more suture passer elevator separators of claim 10, wherein an angle of offset of said first jaw member and said second jaw member relative to said longitudinal axis of said hollow cylindrical rod is at least 45 degrees and wherein a cross section of a tissue penetrating member is substantially circular.

18. The one or more suture passer elevator separators of claim 16, wherein, in said second position, a tissue penetrating member is defined by at least one curved portion having a first radius of curvature greater than or equal to three (3) times a thickness of said tissue penetrating member.

19. The one or more suture passer elevator separators of claim 16, wherein, in said first position, a tissue penetrating member is defined by at least one curved portion having a second radius of curvature selected to be larger than a first radius of curvature.

20. A medical device kit for Achilles tendon repair comprising:
one or more fascial elevator separator(s) comprising a U-shaped paddle guide portion attached to a distal portion of a cylindrical rod and a proximate handle of said cylindrical rod wherein said one or more fascial elevator separator(s) and U-shaped paddle guide portion(s) separate a membrane-like areolar structure known as a Paratenon from an Achilles tendon;
one or more suture passer elevator separators that are tool(s) that maintain separation of said Paratenon from said Achilles tendon and are comprised of a hollow cylindrical rod with an axial and radial axis to which is attached a distal U-shaped paddle guide and wherein an grasping and firing mechanism along with a set of jaws and a needle are located in an inverted position with respect to a longitudinal axis of said hollow cylindrical rod;
one or more large curved suture shuttle passers;
two or more suture bone anchors;
a drill that accommodates various sizes of suture bone anchors;

a length of sutures and/or fiber tape(s) that ensure completion of [complete] said Achilles tendon repair.

21. The medical device kit of claim 20, wherein said kit is utilized for repair of quadriceps and patella tendons.

22. The medical device kit of claim 20, wherein said one or more suture passer elevator separators includes a camera that is located and mounted on an outer portion of said hollow cylindrical rod in order to provide a more accurate determination of where sutures are to be utilized along either a lateral or medial length portion of said Achilles tendon to ensure direct visualization of suture placement and repair.

\* \* \* \* \*